United States Patent [19]
Oudard

[11] Patent Number: 5,326,359
[45] Date of Patent: Jul. 5, 1994

[54] KNEE PROSTHESIS WITH ADJUSTABLE CENTRO-MEDULLARY STEM

[75] Inventor: Jean-Loup Oudard, Saint-Nazaire-Les-Eymes, France

[73] Assignee: Etablissements Tornier, Saint-Ismier, France

[21] Appl. No.: 981,061

[22] Filed: Nov. 24, 1992

[30] Foreign Application Priority Data

Nov. 29, 1991 [FR] France .................. 91 15044

[51] Int. Cl.⁵ .............................................. A61N 1/30
[52] U.S. Cl. ........................................ 623/20; 623/18; 623/23; 606/73
[58] Field of Search ............... 623/18, 20, 23; 606/67, 606/70, 71, 72, 73

[56] References Cited

U.S. PATENT DOCUMENTS

| | | | |
|---|---|---|---|
| 4,098,269 | 7/1978 | Judet | 606/73 |
| 4,883,492 | 11/1989 | Frey et al. | 623/23 |
| 4,923,472 | 5/1990 | Ugolini | 623/20 |
| 4,950,297 | 8/1990 | Elloy et al. | 623/20 |
| 5,133,764 | 7/1992 | Pappas et al. | 623/23 |
| 5,147,406 | 9/1992 | Houston et al. | 623/20 |

FOREIGN PATENT DOCUMENTS

| | | | |
|---|---|---|---|
| 0381352 | 8/1990 | European Pat. Off. | 623/20 |
| 9208424 | 5/1992 | World Int. Prop. O. | 623/20 |

*Primary Examiner*—Randall L. Green
*Assistant Examiner*—Paul Prebilic
*Attorney, Agent, or Firm*—Dowell & Dowell

[57] ABSTRACT

A prosthesis of the knee which includes an articular element including a slideway in which is mounted the base of a bushing which threadingly receives a centro-medullary stem. The centro-medullary stem extends through the bushing so as to be engageable with impressions formed in the slideway to thereby lock the bushing and stem to the slideway.

6 Claims, 2 Drawing Sheets

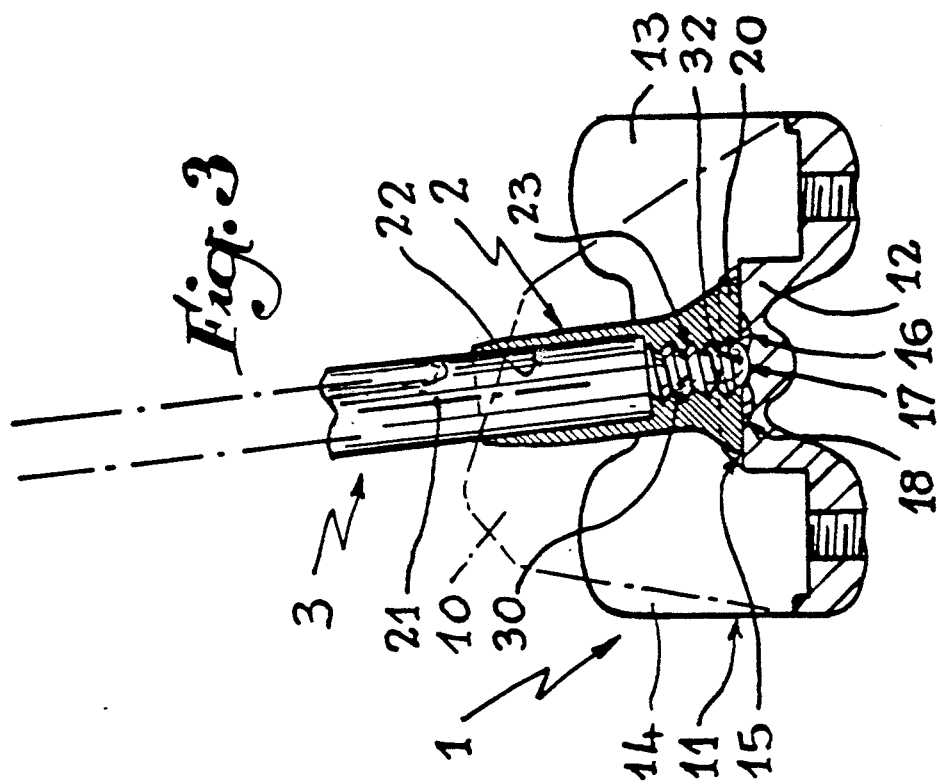
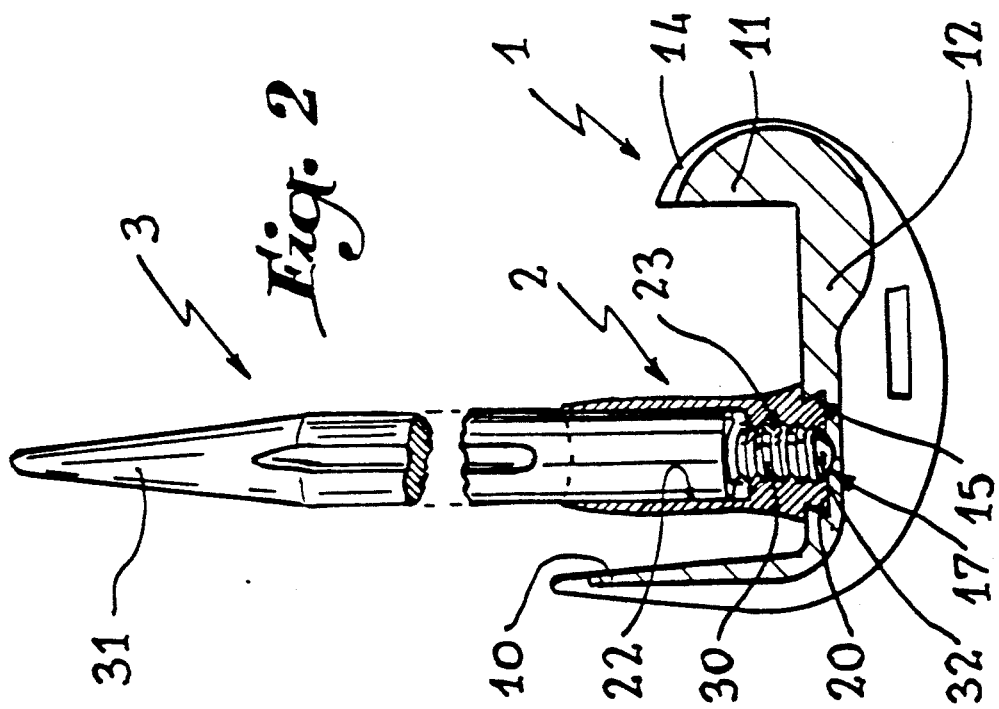

KNEE PROSTHESIS WITH ADJUSTABLE CENTRO-MEDULLARY STEM

BACKGROUND OF THE INVENTION

1. Field of the Invention

The present invention relates to a prosthesis of the knee and more particularly, although not exclusively, to a replacement prosthesis, i.e. one used for replacing part of a total prosthesis of the knee already applied to a patient and which must be replaced for some reason. In the case of replacement, it is often necessary to have more solid anchorages of the femoral and tibial elements, with the result that, for fixing the articular element, a long centro-medullary stem of suitable diameter is generally used.

Such a prosthesis may also be employed from the beginning.

2. History of the Related Art

French Patent No. 74 40575 discloses a prosthesis of the knee comprising two elements associated respectively with the femur and with the tibia, the femur element is made in the form of an incurved plate with two condyles, the plate being associated with a centro-medullary stem, while the second or tibia element includes a tibial plate likewise associated with a centro-medullary stem. The centro-medullary stems, secured to the femoral or tibial pieces, must have different characteristics depending on the surgical cases, with the result that their length, diameter, angulation and positioning with respect to the center must vary. Thus is particularly true for the femoral piece.

If it is desired to respond correctly to the surgical cases in question, the surgeon must have a multitude of implants available, which is extremely expensive.

It is an object of the improvements forming the subject matter of the present invention to overcome these drawbacks and to produce a prosthesis incorporating a plurality of components which enables all the desired dimensions of implants to be obtained economically.

SUMMARY OF THE INVENTION

To that end, the prosthesis according to the invention is characterized in that the articular element include a slideway in which is mounted a bushing of which the geometrical axis is oblique with respect to the base of the sole, while the centro-medullary stem comprises means for assembly on the bushing which cooperate with the slideway to ensure rigid locking of the assembly.

BRIEF DESCRIPTION OF THE DRAWINGS

The invention will be more readily understood on reading the following description with reference to the accompanying drawings, in which:

FIGS. 2 and 3 are longitudinal and transverse sections, respectively, of the prosthesis in the assembled state.

DETAILED DESCRIPTION OF THE DRAWINGS

Figure 1:
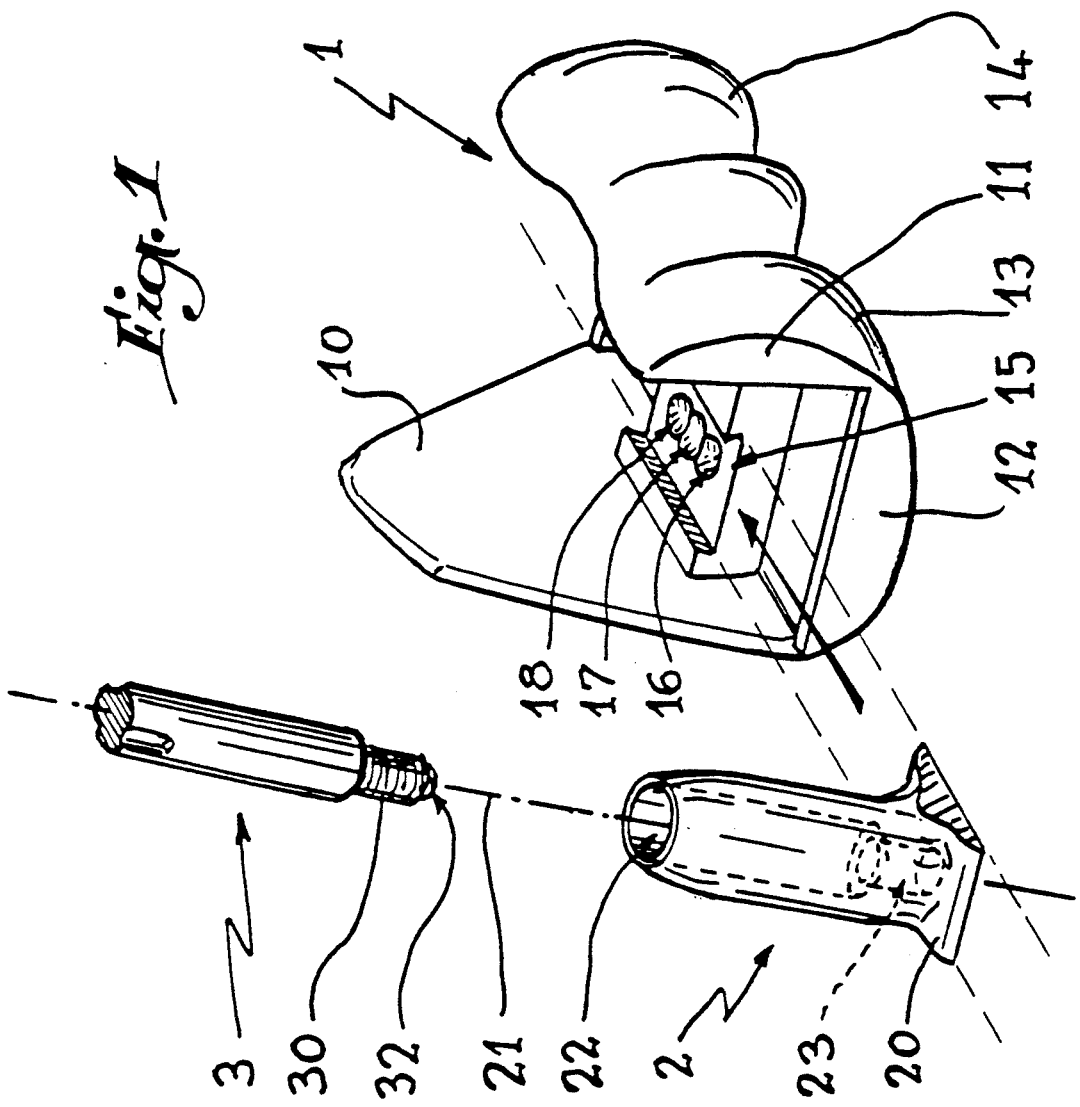
FIG. 1 is an exploded view in perspective of the different components of a prosthesis according to the invention.

Referring now to the drawings, FIG. 1 illustrates the different components of a prosthesis according to the invention, of which the articular element is constituted by a biocompatible femoral piece, it being understood that the invention may equally well be applied to a tibial piece or plate. The femoral plate or piece referenced 1 presents a transverse section generally in the form of a U, i.e. it is formed by a first anterior flange 10 and by a second posterior flange 11, these two flanges being joined by a web 12. The outer face of the two flanges and of the transverse web of the femoral piece 1 includes two lateral condyles 13, 14.

In accordance with the invention, the inner face of the web 12 is provided with a transverse slideway 15 in the form of a dovetail. In the bottom of the slideway 15 and along its longitudinal geometrical axis, a plurality of secant impressions have been formed, three in the present case, 16, 17, 18, which are each roughly in the form of a spherical cap.

The prosthesis according to the invention further include a bushing 2 provided with a base 20 in dovetail form, whose dimensions are such that it may slide and fit precisely in the slideway 15 of the femoral piece 1. It will be observed that the geometrical axis 21 of the bushing 2 is oblique with respect to the base 20. The bushing includes a stepped or countersunk bore including a smooth hole 22 and a tapped hole 23 opening out on the base 20.

The third component of the prosthesis according to the invention is a centro-medullary stem 3 which includes a threaded joining piece 30 having a convex end 32 adapted to screw in the tapped hole 23 of the bushing 2. It will be observed in FIG. 2 that the centro-medullary stem 3 terminates, at its end opposite the joining piece 30, by a pointed part 31.

In order to constitute the prosthesis, the base 20 of the bushing 2 is engaged in the slideway 15, then the stem 3 is fitted in the bushing 2 until its joining piece 30 comes into contact with the tapped hole 23. At that moment, the joining piece 30 of the stem 3 is screwed in the tapped hole 23 until the convex end 32 of the joining piece 30 seats in one of the impressions 16, 17, 18. Efficient tightening ensures a completely rigid assembly.

A prosthesis according to the invention complies simply with the different surgical needs, as each of its components is chosen as a function of the anatomical case for which it is employed. For example, the femoral stem 3 has an adequate diameter and length, and the bushing is chosen from a series depending on the inclination of its axis 21 with respect to its base 20 as a function of the geometry of the patient's hip. It is not necessary to provide right and left bushings since each is reversible with respect to the slideway 15. It is necessary to have a series of right and left femoral pieces, but, by limiting the number of sizes to five, virtually all problems are solved. Finally, there is a possibility of laterally adjusting the position of the bushing, therefore of the stem, due to the presence of a plurality of impressions 16, 17, 18 in the bottom of the slideway 15.

A prosthesis of the knee has thus been produced, and more particularly, but not exclusively, a replacement prosthesis which is capable of responding to the various anatomical desiderata with a very restricted number of parts.

It must, moreover, be understood that the foregoing description has been given only by way of example and that it in no way limits the domain of the invention which would not be exceeded by replacing the details of execution described by any other equivalents.

It will be understood that the slideway 15, provided to be transverse in the foregoing description, may be longitudinal. Moreover, two perpendicular slideways may be made in the web 12. In addition, it goes without saying that the improvements according to the present invention are applicable equally well to a femoral piece and to a tibial plate.

What is claimed is:

1. A prosthesis of the knee comprising a biocompatible plate means having a slideway having a bottom wall, a groove extending along said slideway, a plurality of spaced impressions in said bottom wall, a bushing having a base, said base being slideably receivable within said slideway so as to be engageable within said groove, a bore extending through said bushing and having a tapped portion, a centro-medullary stem having an end and a threaded portion, and threaded portion being securable to said tapped portion of said bushing so as to retain said end of said centro-medullary stem within one of said impressions to thereby secure said centro-medullary stem relative to said plate means.

2. The prosthesis of claim 1 in which said end of said centro-medullary stem is convex so as to seat in said one of said impressions.

3. The prosthesis of claim 1 in which said bore through said bushing is obliquely aligned with respect to said base.

4. The prosthesis of claim 3 in which said bore includes a first section having relatively smooth side walls and said threaded portion being counter sunk with respect to said first section.

5. The prosthesis of claim 1 in which said plate means includes spaced side walls and is generally U-shaped in cross-section.

6. The prosthesis of claim 1 in which said groove is dovetailed in configuration.

* * * * *